United States Patent [19]

Yamashita et al.

[11] Patent Number: 4,990,529
[45] Date of Patent: Feb. 5, 1991

[54] PYRAZOLONE DERIVATIVES FOR TREATING CEREBROVASCULAR DISEASES

[75] Inventors: Hiroyuki Yamashita; Makoto Odate; Hajime Iizuka, all of Kanagawa; Hiroshi Kawazura, Chiba; Yoshio Shiga, Chiba; Hiroshi Namekawa, Chiba, all of Japan

[73] Assignee: Mitsui Toatsu Chemicals, Japan

[21] Appl. No.: 334,249

[22] Filed: Apr. 6, 1989

Related U.S. Application Data

[62] Division of Ser. No. 206,812, Jun. 15, 1988, Pat. No. 4,839,376.

[30] Foreign Application Priority Data

Jun. 17, 1987 [JP] Japan ................... 62-148919

[51] Int. Cl.$^5$ ................. A01N 43/56; A61K 31/415; C07D 231/06; C07D 471/02
[52] U.S. Cl. ..................... 514/406; 424/436; 424/451; 424/464; 544/224; 544/233; 548/100; 548/356; 548/369; 548/374; 548/379; 549/456
[58] Field of Search ............. 514/406; 544/224, 233; 548/100, 356, 369, 374, 379; 549/456; 424/436, 451, 464

[56] References Cited

U.S. PATENT DOCUMENTS

| | | | |
|---|---|---|---|
| 4,003,889 | 1/1977 | Bolton et al. | 548/379 |
| 4,250,185 | 2/1981 | Gaughan | 548/379 |
| 4,677,210 | 6/1987 | Huang | 514/333 |
| 4,780,543 | 10/1988 | Gordon et al. | 548/379 |

OTHER PUBLICATIONS

Bericht 69 1936, 2348–2350 (Beilstein 23 II 26c).
Liebigs Ann, Chem. 458, 210–211 (Beilstein 23 II 165b).
Liebigs Ann, Chem. 458 202,176 (Beilstein 23 II 26c).
JP 60 08.211 (Jan. 17, 1985) (C.A. 102P 216885q).
891112 ED, 11/89, American Chemical Soc. Abstract.

*Primary Examiner*—Thurman K. Page
*Assistant Examiner*—Carlos Azpura
*Attorney, Agent, or Firm*—Nixon & Vanderhye

[57] ABSTRACT

2-Pyrazoline derivatives of the formula (A):

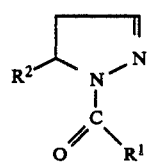

(A)

where $R^1$ is a pyridyl, a pyrazyl or an alkoxyl group; and $R^2$ is a hydrogen atom, an alkyl, a pyridyl, a furyl, phenyl or a substituted phenyl group, and to a process for producing the same. Therapeutic agents for treating cerebrovascular diseases containing, as the active ingredient, a 2-pyrazoline derivative represented by the formula (G):

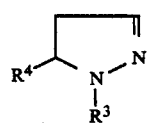

(G)

where $R^3$ is a hydrogen atom, an alkyl, acetyl, an alkoxycarbonyl, an amino, benzoyl, a substituted benzoyl, a pyridylcarbonyl, a furylcabonyl, a thienylcarbonyl, a pyrazylocarbonyl, an N-substituted carbamoyl, an N-substituted thiocarbamoyl, or carboxyl group; and $R^4$ is a hydrogen atom, an alkyl, a pyridyl, a thienyl, a furyl, cyclohexyl, phenyl or a substituted phenyl group or a pharmaceutically acceptable salt thereof. These therapeutic agents cope with cerebral edemas in the acute stage of cerebral apoplexy and regulates the whole-body and intracranial body circulation, thereby protecting ischemic lesions and minimizing the spread to affected parts.

1 Claim, No Drawings

PYRAZOLONE DERIVATIVES FOR TREATING CEREBROVASCULAR DISEASES

CROSS-REFERENCE TO RELATED APPLICATION

This application is a Rule 60 divisional of earlier application Ser. No. 07/206,812, filed June 15, 1988, now U.S. Pat. No. 4839376.

FIELD OF THE INVENTION

This invention relates to new 2-pyrazoline derivatives which inhibit the formation of cerebral edemas in the acute stage of cerebral apoplexy, thereby protecting ischemic lesions and treating nervous disorders after recuperation, to a process for producing the same, and to agents containing the same as active ingredient.

DESCRIPTION OF THE PRIOR ART

The mortality from cerebrovascular diseases (also commonly known by the nonspecific terms of stroke, cerebrovascular accident or CVA) in Japan has been decreasing year by year, now ranking third to follow those from cancers and heart diseases. However, it has been reported that 30 to 60% of the patients with cerebral diseases die in the acute stage, and that many of the patients that survive still suffer from confusion, motor disturbance or sensory insufficiency. It is generally accepted that more than half of the cases of senile dementia in Japan are caused by cerebrovascular diseases.

Most of nervous disorders in the survivors which originate from cerebral ischemia in the acute stage, are difficult to cure in the chronic stage when lesions are inveterate.

Hence, successful treatment in the acute stage is very important with cerebrovascular diseases not only for survival but also for the reduction of lesions remaining after surviving the acute stage.

In the treatment in the acute stage of cerebral apoplexy, emphasis is placed on regulating the whole body and intracranial blood circulation to protect ischemic lesions and minimize the spread of affected parts. Transfusion of a hypertonic solution (e.g., glycerol) and intravenous administration of a steroidal agent have been adopted to suppress cerebral edemas. But the former tends to disturb the balance among electrolytes in the blood, while the latter has side effects, such as hemorrhage of the digestive tract. Barbiturates (e.g., thiopental, pentobarbital and mefobarbital) are also known to protect the brain from cerebral ischemia (Anesthesiology, 47, 285, 1977), and have been applied clinically (Japan Clinics, 43, 185, 1985). But the drugs of this type can be used only in institutions capable of the patient's whole-body control because the effective dose is very close to the dose that causes lowered consciousness and suppressed respiration. In addition, barbiturates have side effects, such as hepatic and renal function insufficiencies.

Recently, Nizofenone has been reported as a drug useful to protect the brain from cerebral ischemia. This helps alleviate consciousness troubles, but has no action to inhibit cerebral edemas (Japan Clinics, 43, 185, 1985).

PROBLEMS TO BE SOLVED BY THE INVENTION

There is a demand for a new drug which inhibits the formation of cerebral edemas in the acute stage of cerebrovascular diseases, thereby protecting ischemic lesions and useful in treating nervous disorders after recuperation.

The object of this invention is to provide new agents comprising 2-pyrazoline derivatives as the pharmacologically active ingredient(s) which are capable of inhibiting the formation of cerebral edemas, protecting ischemic lesions and treating nervous disorders after recuperation.

MEANS TO SOLVE THE PROBLEMS

This invention relates to new 2-pyrazoline derivatives represented by the following general formula (A):

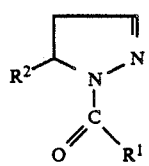

where $R^1$ denotes a pyridyl, pyrazyl or a C 1 to 6 alkoxyl group; and $R^2$ stands for hydrogen atom, a C 1 to 6 alkyl, a pyridyl, a furyl, phenyl or a substituted phenyl group, and pharmaceutically acceptable salts thereof. The invention also includes the use of these compounds in treating cardiovascular diseases and in pharmaceutical compositions containing these compounds.

2-Pyrazoline derivatives of this invention represented by the general formula (A) include the following compounds (the same Compound No. as in Table 1):

1. 1-(3-Pyridylcarbonyl)-5-phenyl-2-pyrazoline
2. 1-(4-Pyridylcarbonyl)-5-phenyl-2-pyrazoline
3. 1-(2-Pyridylcarbonyl)-5-phenyl-2-pyrazoline
4. 1-(3-Pyridylcarbonyl)-5-(2-methoxyphenyl)-2-pyrazoline
5. 1-(3-Pyridylcarbonyl)-5-(3-methoxyphenyl)-2-pyrazoline
6. 1-(3-Pyridylcarbonyl)-5-(4-methoxyphenyl)-2-pyrazoline
7. 1-(3-Pyridylcarbonyl)-5-(2-furyl)-2-pyrazoline
8. 1-Pyrazylcarbonyl-5-phenyl-2-pyrazoline
9. 1-(3-Pyridylcarbonyl)-5-(2-fluorophenyl)-2-pyrazoline
10. 1-(3-Pyridylcarbonyl)-5-(2-methylphenyl)-2-pyrazoline
11. 1-(3-Pyridylcarbonyl)-5-(4-chlorophenyl)-2-pyrazoline
12. 1-(3-Pyridylcarbonyl)-2-pyrazoline
13. 1-(3-Pyridylcarbonyl)-5-(3-methylphenyl)-2-pyrazoline
14. 1-(3-Pyridylcarbonyl)-5-(4-methylphenyl)-2-pyrazoline
15. 1-(3-Pyridylcarbonyl)-5-(2-chlorophenyl)-2-pyrazoline
16. 1-(3-Pyridylcarbonyl)-5-(3-pyridyl)-2-pyrazoline
17. 1-(3-Pyridylcarbonyl)-5-methyl-2-pyrazoline
18. 1-(2-Pyridylcarbonyl)-5-methyl-2-pyrazoline
19. 1-Pyrazylcarbonyl-5-methyl-2-pyrazoline
20. 1-(3-Pyridylcarbonyl)-5-ethyl-2-pyrazoline
21. 1-(3-Pyridylcarbonyl)-5-propyl-2-pyrazoline
22. 1-(3-Pyridylcarbonyl)-5-isopropyl-2-pyrazoline
23. 1-(3-Pyridylcarbonyl)-5-cyclopropyl-2-pyrazoline
24. 1-(3-Pyridylcarbonyl)-5-butyl-2-pyrazoline
25. 1-Ethoxycarbonyl-5-phenyl-2-pyrazoline
26. 1-Ethoxycarbonyl-5-(3-pyridyl)-2-pyrazoline 27. 1-Ethoxycarbonyl-5-(2-chlorophenyl)-2-pyrazoline
28. 1-Ethoxycarbonyl-5-methyl-2-pyrazoline
29. 1-Butoxycarbonyl-5-methyl-2-pyrazoline
30. 1-Methoxycarbonyl-5-ethyl-2-pyrazoline These 2-pyrazoline derivatives can be prepared by reaction of an α,β-unsaturated aldehyde of the following general formula (B):

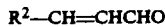

R²—CH=CHCHO                    (B)

where R² is as defined for the general formula (A) with hydrazine to form a 5-substituted-2-pyrazoline represented by the following general formula (C):

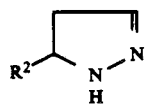
(C)

where R² is as defined for the general formula (A), followed by reaction with an acid chloride represented by the following general formula (D):

R¹—COCl                        (D)

wherein R¹ is as defined for the general formula (A). In the first step, however, hydrazine used to be employed in large excess to prevent the formation of by-product azines. Our studies on this reaction revealed that the amount of hydrazine can be reduced to 1.0 to 1.5 equivalent proportions if the reaction is carried out in the presence of acetic acid ; preferably in an amount of 0.5 to 2 equivalent proportions based on the amount of hydrazine. The reaction may be allowed to proceed in a suitable solvent, such as water, methanol and ethanol.

The α,β-unsaturated aldehydes not otherwise readily available commercially can be synthesized by reaction of an aldehyde of the following general formula (E),

R¹—CHO                         (E)

where R¹ is as defined for the general formula (A) with diethylphosphonoacetonitrile to form an α,β-unsaturated nitrile represented by the following general formula (F):

R¹—CH=CHCH                     (F)

where R¹ is as for the general formula (A), followed by reaction with diisobutylaluminum hydride.

The pharmaceutically active agents of this invention for treating cerebrovascular diseases also contain as the active ingredient, in addition to a compound defined above (selected from compounds No. 1 to No. 30 listed above), a compound selected from those listed below.

31. 5-Phenyl-2-pyrazoline
32. 5-(4-Chlorophenyl)-2-pyrazoline
33. 5-(3-Chlorophenyl)-2-pyrazoline
34. 5-(2-Chlorophenyl)-2-pyrazoline
35. 5-(4-Methylphenyl)-2-pyrazoline
36. 5-(3-Methylphenyl)-2-pyrazoline
37. 5-(2-Methylphenyl)-2-pyrazoline
38. 5-(4-Methoxyphenyl)-2-pyrazoline
39. 5-(3-Methoxyphenyl)-2-pyrazoline
40. 5-(2-Methoxyphenyl)-2-pyrazoline
41. 5-(4-Fluorophenyl)-2-pyrazoline
42. 5-(3-Fluorophenyl)-2-pyrazoline
43. 5-(2-Fluorophenyl)-2-pyrazoline
44. 5-(4-Trifluoromethylphenyl)-2-pyrazoline
45. 5-(3-Trifluoromethylphenyl)-2-pyrazoline
46. 5-(2-Trifluoromethylphenyl)-2-pyrazoline
47. 5-(4-Hydroxyphenyl)-2-pyrazoline
48. 5-(3-Hydroxyphenyl)-2-pyrazoline
49. 5-(2-Hydroxyphenyl)-2-pyrazoline
50. 5-Methyl-2-pyrazoline
51. 5-Cyclohexyl-2-pyrazoline
52. 5-(4-Pyridyl)-2-pyrazoline
53. 5-(3-Pyridyl)-2-pyrazoline
54. 5-(2-Pyridyl)-2-pyrazoline
55. 1-Methyl-5-phenyl-2-pyrazoline
56. 1-Acetyl-5-phenyl-2-pyrazoline
57. Sodium 5-phenyl-2-pyrazoline-1-carboxylate
58. 1-Amino-5-phenyl-2-pyrazoline
59. 1-Benzoyl-5-phenyl-2-pyrazoline
60. 1-(4-Trifluoromethylbenzoyl)-5-phenyl-2-pyrazoline
61. 1-Benzoylmethyl-5-phenyl-2-pyrazoline
62. 1-Cyclohexylcarbonyl-5-phenyl-2-pyrazoline
63. 1-(2-Furylcarbonyl)-5-phenyl-2-pyrazoline
64. 1-(2-Thienylcarbonyl)-5-phenyl-2-pyrazoline
65. 1-[N-(3-pyridyl)carbamoyl]-5-phenyl-2-pyrazoline
66. 1-[N-(3-pyridyl)thiocarbamoyl]-5-phenyl-2-pyrazoline These pharmacologically active compounds (1–66) suitable for treating cerebrovascular disease are altogether represented by the following formula (G):

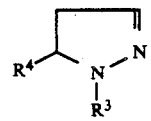
(G)

where R³ denotes hydrogen atom, a C 1 to 6 alkyl, acetyl, a C 1 to 6 alkoxycarbonyl, amino, benzoyl, a substituted benzoyl, a pyridylcarbonyl, a furylcabonyl, a thienylcarbonyl, pyrazylcarbonyl an N-substituted carbamoyl, an N-substituted thiocarbamoyl, or carboxyl group: and R⁴ stands for hydrogen atom, a C 1 to 6 alkyl, a pyridyl, a thienyl, a furyl, cyclohexyl, phenyl or a substituted phenyl group.

As examples of the salts of the compounds of this invention, there may be mentioned hydrochlorides, phosphates, fumarates and maleates.

The above-mentioned -pyrazoline derivatives and salts thereof may be supplied to the patient in various pharmaceutical presentations, such as in the form of parenteral injections, suppositories or oral preparations. Alternatively, these may also be transfused as a 20% glycerol solution as commonly used for the treatment of cerebral edemas.

The preferable dose of the aforementioned 2-pyrazoline derivatives and salts thereof in the acute stage of cerebrovascular diseases is 0.1 to 2.0 g/day. When applied as a parenteral injection, for example, 10 ml of a parenteral solution containing 3% of a 2-pyrazoline derivative mentioned above or a salt thereof may be intravenously injected several times a day, or 2 ml of a solution containing 15% of that compound may be intramuscularly injected several times a day. Suppositories can be prepared by dispersing or dissolving a fine powder of a 2-pyrazoline derivative mentioned above or a salt thereof in a base material, such as Witebsol ®, preferably in an amount of 1 to 10%. In actual practice, for example, three grams of a suppository containing 5 to 10% of the active ingredient may be applied several times a day. For oral administration, tablets and capsules can be prepared by mixing 0.1 to 2.0 g of a 2-pyrazoline derivative mentioned above or a salt thereof with pharmaceutically acceptable vehicle, excipient, binder and stabilizer by commonly used techniques. The oral agents thus prepared may be administered several times a day depending on the conditions of patients.

The following Examples will further illustrate the invention.

EXAMPLE 1

1-(3-Pyridylcarbonyl)-5-phenyl-2-pyrazoline (Compound No. 1)

(1) Cinnamonitrile

Four grams of 60% sodium hydride was suspended in 100 ml tetrahydrofuran, and 17.1 g of diethylphosphonoacetonitrile was added with ice cooling. To the resulting solution, was added dropwise a solution of 10.6 g benzaldehyde in 80 ml tetrahydrofuran, and the mixture was stirred for one hour. After admixing 50 ml water, the organic layer was collected, dried over anhydrous sodium sulfate and concentrated. Distillation of the concentrate under reduced pressure (102°–106° C./6 mmHg) gave 8.9 g yield: 69.0%) of cinnamonitrile.

(2) Cinnamaldehyde

To a solution of 8 g cinnamonitrile in 100 ml tetrahydrofuran, was added dropwise 50 ml of a 1.5M toluene solution of diisobutylaluminum hydride with ice cooling, and the resulting mixture was stirred at room temperature for two hours. The reaction mixture was slowly poured to 200 ml ice water, hydrochloric acid was then added to dissolve the aluminum hydroxide formed, and the organic layer was collected and dried. Distillation of the dried solution under reduced pressure gave 5.2 g (yield: 63.6%) of cinnamaldehyde.

(3) 5-Phenyl-2-pyrazoline

Acetic acid (2.7 g) was added dropwsie to a solution of 2.3 g hydrazine monohydrate in 5 ml ethanol with ice cooling. The resulting mixture was heated under reflux, 5 9 of cinnamaldehyde was added dropwise, and heating under reflux was further continued for three hours. After cooling with ice, 3.5 ml of conc. ammonia was added dropwise, and the mixture was extracted twice with 20 ml chloroform. The extract was dried over anhydrous magnesium sulfate, and the dried solution was distilled under reduced pressure (110°–115° C./6 mmHg), affording 3.8 g (yield: 69 %) of 5-phenyl-2-pyrzoline.

(4) 1-(3-Pyridylcarbonyl)-5-phenyl-2-pyrazoline

A mixture of 5-phenyl-2-pyrazoline (2.9 g) and triethylamine (4 g) was added dropwise with ice cooling to a suspension of nicotine chloride hydrochloride (4 g) in 20 ml chloroform the resulting mixture was stirred for 15 minutes, washed with water and concentrated, and the concentrate was purified by silica gel chromatography (chloroform/methanol = 100/1), giving 4.3 g (yield: 86%) of pure product. M.p. 100°–102° C.; NMR (CDCl$_3$): 2.9–3.8 (2H, m), 5.61 (1H, dd, J=5, 12 Hz), 7.03 (1H, t, J=2 Hz), 7.31 (5H, s), 7.28 (1H, m), 8.15 (1H, dt, J=8, 2 Hz), 8.68 (1H, dd, J=2, 6 Hz), 9.13 (1H, d, J=2 Hz).

EXAMPLES 2 THROUGH 22

Compounds No. 2 through No. 24, prepared in the same manner as in Example 1, are shown in Table 1.

EXAMPLE 23

1-Ethoxycarbonyl-5-phenyl-2-pyrazoline (Compound No. 25)

Triethylamine (2.1 g) was added to a solution of 2.92 g 5-phenyl-2-pyrazoline in 50 ml chloroform, and the mixture was stirred with ice cooling. To the resulting solution, was added dropwise 2.17 g ethyl chloroformate, and the mixture was stirred for one hour. After addition of 50 ml water, the mixture was extracted with 50 ml chloroform, the extract was dried, the dried solution was concentrated, and the residue was purified by silica gel chromatography (chloroform/methanol = 100/1), giving 2.7 g (yield: 62%) of pure product as oil. NMR (DMSO-d$_6$): 1.21 (3H, t, J=6 Hz), 2.6–3.7 (2H, m), 4.18 (2H, q, J=6 Hz), 5.22 (1H, dd, J=6, 12 Hz), 6.92 (1H, t, J=2 Hz), 7.1–7.5 (5H, m).

EXAMPLES 24 THROUGH 28

Compounds No. 26 through No. 30, prepared in the same manner as in Example 23, are shown in Table 1.

EXAMPLES 29 THROUGH 33

Compound No. 59, No. 60, No. 62, No. 63 and No. 64, prepared in the same manner as in Example 1, are shown in Table 1.

| Example No. | Compound No. | Structure | Properties m.p. NMR(CDCl$_3$) δ = |
| --- | --- | --- | --- |
| 2 | 2 | (phenyl-pyrazoline-CO-pyridine structure) | mp 142–143° C., NMR 2.75–3.65 (2H,m), 5.58 (1H,dd,J=5,12Hz), 7.06 (1H,t,J=2Hz), 7.34 (5H,s), 7.70 (2H,d,J=5Hz), 8.73 (2H,d,J=5Hz) |
| 3 | 3 | (phenyl-pyrazoline-CO-pyridine structure) | mp 130–131° C., NMR 2.7–3.7 (2H,m), 5.67 (1H,dd,J=6,12Hz), 7.07 (1H,t,J=2Hz), 7.35 (5H,s), 7.2–7.9 (3H,m), 8.76 (1H,d,J=4Hz) |

-continued

| Example No. | Compound No. | Structure | Properties m.p. NMR(CDCl$_3$) δ = |
|---|---|---|---|
| 4 | 4 | 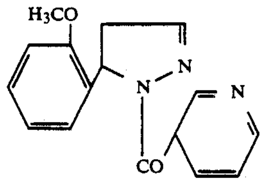 | mp 93–95° C., NMR 2.5–3.8 (2H,m), 3.90 (3H,s), 5.86 (1H,dd,J=5,12Hz), 6.7–7.5 (6H,m), 8.25 (1H,dt,J=2,8Hz), 8.70 (1H,dd,J=2,5Hz), 9.17 (1H,d,J=2Hz) |
| 5 | 5 | 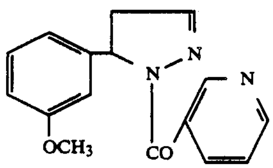 | Oil, NMR 2.5–4.0 (2H,m), 3.85 (3H,s), 5.79 (1H,dd,J=5,12Hz), 6.7–7.5 (6H,m), 8.25 (1H,dt,J=2,8Hz), 8.70 (1H,dd,J=2,8Hz), 9.17 (1H,J=2Hz) |
| 6 | 6 | 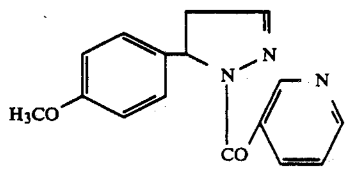 | mp 83–85° C., NMR 2.7–4.2 (2H,m), 3.81 (3H,s), 5.60 (1H,dd,J=5,12Hz), 6.8–7.5 (6H,m), 8.25 (1H,dt,J=2,8Hz), 8.72 (1H,dd,J=2,8Hz), 9.16 (1H,d,J=2Hz) |
| 7 | 7 | 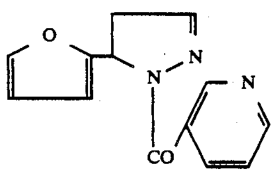 | mp 91–93° C., NMR 3.20 (1H,d,J=2Hz), 3.34 (1H,t,J=2Hz), 5.75 (1H,dd,J=8,10Hz), 6.25–6.50 (2H,m), 7.07 (1H,tt,J=2Hz), 7.1–7.5 (2H,m), 8.23 (1H,dt,J=8,2Hz), 8.70 (1H,dd,J=2,5Hz), 9.13 (1H,d,J=2Hz) |
| 8 | 8 | 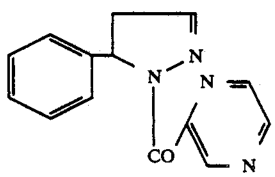 | mp 103–105° C., NMR 2.6–3.6 (2H,m), 5.60 (1H,dd,J=5,12Hz), 7.08 (1H,t,J=2Hz), 7.32 (5H,s), 8.64 (2H,s), 8.96 (1H,s) |
| 9 | 9 | 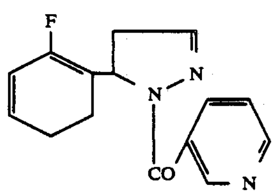 | mp 85–87° C., NMR 2.5–3.7 (2H,m), 5.83 (1H,dd,J=6,11Hz), 7.0–7.5 (6H,m), 8.27 (1H,dt,J=2,12Hz), 8.77 (1H,dd,J=2,5Hz), 9.22 (1H,d,J=2Hz) |
| 10 | 10 | 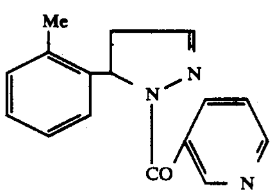 | mp 111–113° C., NMR 2.48 (3H,s), 2.5–3.8 (2H,m), 5.78 (1H,dd,J=5,12Hz), 7.04 (1H,t,J=2Hz), 7.0–7.5 (5H,m), 8.23 (1H,dt,J=2,8Hz), 8.72 (1H,dd,J=2,5Hz), 9.20 (1H,d,J=2Hz) |
| 11 | 11 | 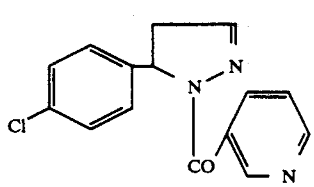 | Oil, NMR 2.5–3.9 (2H,m), 5.57 (1H,dd,J=5,12Hz), 7.02 (1H,t,J=2Hz), 7.02 (1H,t,J=2Hz), 7.27 (4H,s), 7.3 (1H,m), 8.20 (1H,dt,J=2,7Hz), 8.65 (1H,dd,J=2,5Hz), 9.10 (1H,d,J=2Hz) |

-continued

| Example No. | Compound No. | Structure | Properties m.p. NMR(CDCl₃) δ = |
|---|---|---|---|
| 12 | 12 | 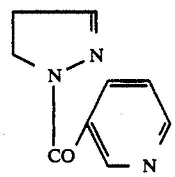 | mp 81–82° C., NMR 2.8–3.4 (2H,m), 3.7–4.3 (2H,m), 7.02 (1H,t,J=2Hz), 7.35 (1H,dd,J=4,8Hz), 8.23 (1H,dt,J=2,8Hz), 8.70 (1H,dd,J=2,4Hz), 9.14 (1H,d,J=2Hz) |
| 13 | 13 | 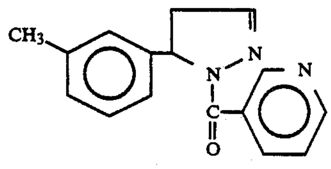 | Oil, NMR 2.30 (3H,s), 2.5–3.8 (2H,m), 5.77 (1H,dd,J=5,12Hz), 7.03 (1H,t,J=2Hz) 7.2–7.4 (5H,m), 8.23 (1H,dt,J=2,8Hz), 8.75 (1H,dd,J=2,5Hz), 9.20 (1H,d,J=2Hz) |
| 14 | 14 | 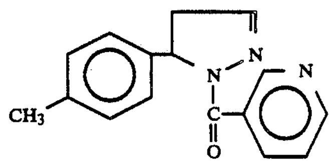 | mp 97–98° C., NMR 2.33 (3H,sm), 2.5–3.8 (2H,m), 5.60 (1H,dd,J=5,12Hz), 7.01 (1H,t,J=2Hz), 7.1–7.5 (5H,m), 8.18 (1H,td,J=2,8Hz), 8.67 (1H,dd,J=2,5Hz), 9.13 (1H,d,J=2Hz) |
| 15 | 15 | 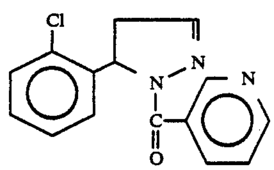 | mp 85–87° C., NMR 2.5–3.8 (2H,m), 6.00 (1H,dd,J=5,11Hz), 7.08 (1H,t,J=2Hz), 7.2–7.6 (5H,m), 8.37 (1H,dt,J=2,8Hz), 8.81 (1H,dd,J=2,5Hz), 9.28 (1H,d,J=2Hz) |
| 16 | 16 | 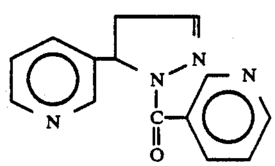 | mp 86–89° C., NMR 2.6–4.0 (2H,m), 5.65 (1H,dd,J=5,11Hz), 7.09 (1H,t,J=2Hz), 7.2–9.2 (8H,m) |
| 17 | 17 | 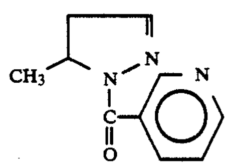 | Oil, NMR 1.42 (3H,d,J=7Hz), 2.4–3.4 (2H,m), 4.5–5.0 (1H,m), 6.97 (1H,t,J=2Hz), 7.38 (1H,dd,J=5,8Hz), 8.16 (1H,dt,J=8,2Hz), 8.64 (1H,dd,J=2,4Hz), 9.02 (1H,d,J=4Hz) |
| 18 | 18 | 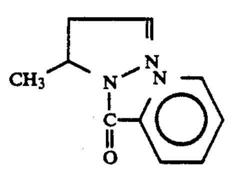 | Oil, NMR 1.47 (3H,d,J=6Hz), 2.3–3.5 (2H,m), 4.5–5.1 (1H,m), 6.98 (1H,t,J=2Hz), 7.2–8.1 (3H,m), 8.73 (1H,dt,J=4,1Hz) |
| 19 | 19 | 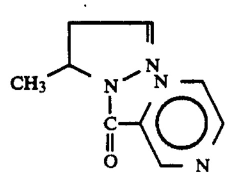 | mp 81–83° C., NMR 1.51 (3H,d,J=6Hz), 2.3–3.6 (2H,m), 4.5–5.1 (1H,m), 7.07 (1H,t,J=2Hz), 8.73 (2H,s), 9.00 (1H,s) |
| 20 | 20 | 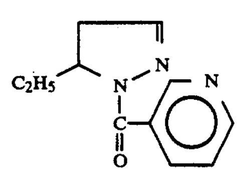 | Oil, NMR 0.94 (3H,t,J=7Hz), 1.1–2.2 (2H,m), 4.3–4.8 (1H,m), 2.3–3.3 (2H,m), 6.90 (1H,t,J=2Hz), 7.27 (1H,dd,J=4,8Hz), 8.10 (1H,dt,J=8,2Hz), 8.62 (1H,dd,J=2,4Hz), 9.00 (1H,d,J=2Hz) |

-continued

| Example No. | Compound No. | Structure | Properties m.p. NMR(CDCl$_3$) δ = |
|---|---|---|---|
| 21 | 21 | (pyrazoline with CH$_3$CH$_2$CH$_2$ substituent, N-C(=O)-pyridyl) | Oil, NMR 0.98 (3H,t,J=6Hz), 0.9-2.3 (4H,m), 2.3-3.5 (2H,m), 4.4-5.0 (1H,m), 6.97 (1H,t,J=2Hz), 7.32 (1H,dd,J=4,7Hz), 8.17 (1H,dt,J=2,7Hz), 8.69 (1H,dd,J=2,4Hz), 9.10 (1H,d,J=2Hz) |
| 22 | 24 | (pyrazoline with CH$_3$CH$_2$CH$_2$CH$_2$ substituent, N-C(=O)-pyridyl) | Oil, NMR 0.8-2.2 (9H,m), 2.4-3.5 (2H,m), 4.5-5.0 (1H,m), 6.99 (1H,t,J=2Hz), 7.41 (1H,dd,J=5,8Hz), 8.20 (1H,dt,J=8,2Hz), 8.74 (1H,dd,J=2,5Hz), 9.18 (1H,d,J=2Hz) |
| 24 | 26 | (pyrazoline with pyridyl substituent, N-C(=O)-O-C$_2$H$_5$) | Oil, NMR 1.21 (3H,t,J=6Hz), 2.6-3.7 (2H,m), 4.18 (2H,q,J=6Hz), 5.22 (1H,dd,J=6,12Hz), 6.92 (1H,t,J=2Hz), 7.1-7.5 (5H,m) |
| 25 | 27 | (pyrazoline with 2-chlorophenyl substituent, N-C(=O)-O-C$_2$H$_5$) | mp 54-56° C., NMR 1.22 (3H,t,J=7Hz), 2.40 (3H,s), 2.5-3.8 (2H,m), 4.23 (2H,q,J=7Hz), 5.47 (1H,dd,J=6,12Hz), 6.94 (1H,t,J=2Hz), 7.1-7.4 (4H,m) |
| 26 | 28 | (pyrazoline with CH$_3$ substituent, N-C(=O)-O-C$_2$H$_5$) | Oil, NMR 2.30 (3H,s), 1.30 (3H,d,J=6Hz), 1.40 (3H,t,J=6Hz), 2.2-3.5 (2H,m), 4.33 (2H,q,J=6Hz), 4.1-4.8 (1H,m), 6.90 (1H,t,J=2Hz) |
| 27 | 29 | (pyrazoline with CH$_3$ substituent, N-C(=O)-O-CH$_2$CH$_2$CH$_2$CH$_3$) | Oil, NMR 0.7-2.0 (7H,m), 1.31 (3H,d,J=6Hz), 2.2-3.5 (2H,m), 4.28 (2H,t,J=7Hz), 4.1-4.8 (1H,m), 8.92 (1H,t,J=2Hz) |
| 28 | 30 | (pyrazoline with CH$_3$CH$_2$ substituent, N-C(=O)-O-CH$_3$) | Oil, NMR 0.7-2.0 (5H,m), 2.2-3.5 (2H,m), 3.88 (3H,s), 4.0-4.6 (1H,m), 6.92 (1H,t,J=2Hz) |
| 29 | 59 | (pyrazoline with phenyl substituent, N-C(=O)-phenyl) | mp 105-106° C., NMR 2.6-3.5 (1H,m), 5.56 (1H,dd,J=5,12Hz), 6.92 (1H,t,J=2Hz), 7.2-8.0 (10H,m) |
| 30 | 60 | (pyrazoline with phenyl substituent, N-C(=O)-C$_6$H$_4$-CF$_3$) | mp 107-108° C., NMR 2.7-3.7 (2H,m), 5.59 (1H,dd,J=6,12Hz), 7.00 (1H,t,J=2Hz), 7.32 (5H,s), 7.63 (1H,d,J=8Hz), 7.96 (1H,d,J=8Hz) |

-continued

| Example No. | Compound No. | Structure | Properties m.p. NMR(CDCl₃) δ = |
|---|---|---|---|
| 31 | 62 | 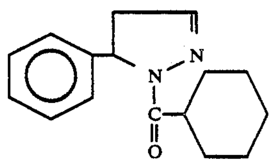 | mp 85–86° C., NMR 1.0–2.0 (10H,m), 2.6–3.6 (2H,m), 3.10 (1H,m), 5.35 (1H,dd,J=5,12Hz), 6.88 (1H,t,J=2Hz), 7.0–7.48 (5H,m) |
| 32 | 63 | 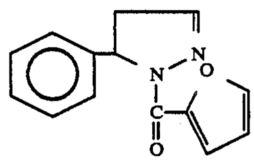 | mp 136–137° C., NMR 2.6–3.6 (2H,m), 5.52 (1H,dd,J=5,12Hz), 6.97 (1H,t,J=2Hz), 7.12 (5H,s), 7.15–7.60 (3H,m) |
| 33 | 64 | 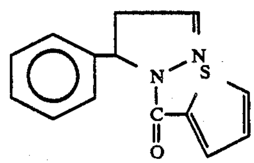 | mp 131–132° C., NMR 2.6–3.6 (2H,m), 5.52 (1H,dd,J=5,12Hz), 7.03 (1H,t,J=2Hz), 7.05 (1H,m), 7.28 (5H,s), 7.54 (1H,d,J=4Hz), 8.10 (1H,d,J=4Hz) |

EXAMPLE 34

1-Methyl-5-phenyl-2-pyrazoline (Compound No. 55)

Cinnamaldehyde (13.2 g) was added dropwise to a solution of 5 g methylhydrazine in 50 ml ethanol, and the mixture was heated under reflux for six hours. At the end of reaction, the solvent was distilled off under reduced pressure, and the residue was dissolved in 50 ml ether. The solution was washed with water and concentrated, and the concentrate was distilled under reduced pressure, giving 3.6 g (yield: 22%) of pure product. B.p.: 95°–105° C./5 mmHg; NMR (CDCl₃): 2.2–3.3 (2H, m), 2.65 (3H, s), 3.76 (1H, dd, J=10, 14 Hz), 6.51 (1H, t, J=2 Hz ], 7.1–7.6 (5H, m).

EXAMPLE 35

Sodium 5-phenyl-2-pyrazoline-1-carboxylate (Compound No. 57)

Ethyl chloroformate (12 g) was added dropwise under ice cooling to a solution of 14.6 g 5-phenyl-2-pyrazoline and 12 g triethylamine in 100 ml chloroform, and the mixture was stirred at room temperature for three hours. The reaction mixture was washed with 3% hydrochloric acid and 3% aqueous solution of sodium bicarbonate in that order and then dried over anhydrous sodium sulfate. The solvent was distilled off from the dried solution, and the oily residue thus obtained (20 g) was dissolved in 80 ml ethanol. To this ethanolic solution, was added 10 ml of 40% aqueous solution of caustic soda, the mixture was stirred at room temperature for one hour, and the crystals which precipitated out were collected by filtration and dried under reduced pressure, affording 12 g of pure product. M.p.: 210° C. (dec.); NMR (D₂O): 2.6–3.4 (2H, m), 4.7 (1H, dd, J=12,5 Hz), 7.14 (1H, t, J=2 Hz), 7.40 (5H, s).

EXAMPLE 36

1-[N-(3-pyridyl)carbamoyl]-5-phenyl-2-pyrazoline (Compound No. 65)

Nicotinic acid hydrazide (18 g) was added in small portions with ice cooling to 22 ml concentrated hydrochloric acid, and 30 ml of aqueous solution of 18 g sodium nitrite was then added dropwise while maintaining the temperature at 0° C. or lower. The mixture was stirred at 0° C. for 15 minutes and extracted with ether, the extract was washed with an aqueous solution of sodium bicarbonate and dried over anhydrous sodium sulfate, and the solvent was distilled off from the dried solution, giving 16 g of nicotinic acid azide.

This was dissolved in 100 ml benzene, the solution was heated under reflux for five hours, insoluble matter filtered off, and the filtrate was concentrated under reduced pressure, giving 13 g of 3-pyridyl isocyanate. A solution of 7.5 g of this compound in 20 ml ethyl acetate was addaed dropwise to a solution of 7.3 g 5-phenyl-2-pyrazoline in 50 ml ethyl acetate, and the mixture was stirred at room temperature for 30 minutes and then concentrated. The concentrate was purified by silica gel chromatography (chloroform/methanol=50/1), affording 2.1 g (yield: 79%) of pure product. M.p.: 104°–106° C; NMR (CDCl₃): 2.6–3.8 (2H, m), 5.38 (1H, dd, J=5, 12 Hz), 6.90 (1H, t, J=2 Hz), 7.30 (5H, s), 7.20 (1H, m), 8.0–8.4 (2H, m), 8.2 (1H, b), 8.58 (1H, d, J=2 Hz).

EXAMPLE 37

1-[N-(3-pyridyl)thiocarbamoyl]-5-phenyl-2-pyrazoline (Compound No. 66)

To a solution of 9.4 g 3-aminopyridine and 7.6 g carbon disulfide in 100 ml benzene, was added dropwise 14 ml triethylamine, the mixture was stirred at room temperature for three hours, and the two separate layers thus formed were allowed to stand overnight. The benzene layer was removed by decantation, the oily product was washed four times with 30 ml ether, and the solvent was distilled off under reduced pressure, affording triethylammonium (3-pyridyl)dithiocarbamate. This crude salt was dissolved in 75 ml chloroform, 14 ml triethylamine was added, and the resulting solution was cooled in ice. Ethyl chloroformate (10.2 ml) was then added dropwise, the reaction was allowed to proceed at room temperature for one hour, and the reaction mixture was washed with 50 ml water, dried over anhydrous sodium sulfate and concentrated under reduced pressure, giving 13.2 g of rude 3-pyridyl isothiocyanate as oil.

A solution of this oil (7.5 g) in 20 ml chloroform was added dropwise to a solution of 7.3 g 5-phenyl-2-pyrazoline in 50 ml chloroform, the mixture was stirred for 30 minutes and then concentrated, and the concentrate was purified by silica gel chromatography (chloroform/methanol=50/1), giving 8.0 g (yield: 57%) of pure product. M.p.: 156°–158° C.; NMR (CDCl$_3$): 2.6–3.8 (2H, m), 5.83 (1H, dd, J=5, 11 Hz), 7.07 (1H, t, J=2 Hz), 7.30 (5H, s), 7.25 (1H, m), 8.2–8.5 (2H, m), 8.67 (1H, d, J=2 Hz), 9.26 (1H, b).

EXAMPLE 38

(Action upon ischemic cerebral edemas of rats caused by occlusion of the middle cerebral artery)

Middle cerebral artery occlusion of rats was induced by the method of Tamura et al. (J. Cerebral Blood Flow and Metabolism, 1981, 53–60): the left middle cerebral artery of Wistar rats (8 to 10 weeks old) was occluded under anesthesia with 2% halothane. The compound being tested was suspended in 0.5% aqueous solution of CMC, and this suspension was intraperitoneally injected to each rat immediately after occlusion, and 8 hours and 16 hours later (a total of three times). Twenty-four hours after occlusion, each of the treated rats was sacrificed, the brain was excised, and the water content of hemispheres were determined by weighing the hemispheres before and after drying at 110° C. to the constant weight. On the other hand, the rats of the control group were subjected to arterial occlusion in the same way as above, followed by intraperitoneal injection of physiological saline three times a day. The cerebral edema inhibition rate of each compound was calculated from the following equation, $$\text{Edema inhibition (\%)} = \left\{ 1 - \frac{(SL - SR)/SR}{(CL - CR)/CR} \right\} \times 100$$

where CL and CR represent the water contents of left and right hemispheres of the control group and SL and SR the water contents of left and right hemispheres of the treated group.

Acute toxicity (LD50) was determined by intraperitoneal injection of a compound being tested to mice and by calculation from the mortality 48 hours after injection by the usual method. These results are summarized in Table 2.

TABLE 2

| Compound No. | Dose (mg/Kg) | Cerebral Edema Inhibition Rate (%) | Acute Toxicity (LD50, mg/Kg) |
|---|---|---|---|
| 1 | 30 | 36.0 | 600 |
| 2 | 30 | 30.5 | 630 |
| 3 | 30 | 15.7 | 560 |
| 4 | 30 | 28.3 | 610 |
| 5 | 30 | 20.7 | 630 |
| 6 | 30 | 19.3 | 830 |
| 7 | 30 | 31.2 | 1100 |
| 8 | 25 | 33.0 | 710 |
| 9 | 25 | 29.1 | 830 |
| 10 | 25 | 31.3 | 610 |
| 11 | 25 | 29.3 | 710 |
| 17 | 25 | 34.0 | 850 |
| 22 | 50 | 27.2 | 830 |
| 30 | 25 | 29.1 | 740 |
| 31 | 25 | 32.0 | 540 |
| 34 | 25 | 29.1 | 600 |
| 37 | 25 | 30.4 | 680 |

TABLE 2-continued

| Compound No. | Dose (mg/Kg) | Cerebral Edema Inhibition Rate (%) | Acute Toxicity (LD50, mg/Kg) |
|---|---|---|---|
| 40 | 25 | 25.7 | 560 |
| 42 | 25 | 23.9 | 710 |
| 45 | 25 | 30.4 | 630 |
| 52 | 25 | 21.8 | 540 |
| 53 | 25 | 16.7 | 600 |
| 56 | 25 | 15.9 | 1100 |
| 25 | 50 | 27.2 | 830 |
| 57 | 50 | 18.6 | 710 |
| 59 | 30 | 21.7 | 600 |
| 60 | 30 | 20.9 | 810 |
| 61 | 30 | 16.7 | 540 |
| 62 | 30 | 15.3 | 630 |
| 63 | 30 | 26.1 | 710 |
| 64 | 30 | 28.5 | 830 |
| 65 | 25 | 27.1 | 630 |
| 66 | 25 | 18.9 | 560 |

EXAMPLE 39

(Action against cerebral infarction of rats caused by occlusion of the middle cerebral artery)

Cerebral infarction of rats caused by occlusion of the middle cerebral artery was measured by the method of Tamura et al. (Japan Clinics, 43, 185, 1985). The middle cerebral artery of rats was artificially occluded, the compound being tested was suspended in 0.5% aqueous solution of CMC, and this suspension was intraperitoneally injected to each rat immediately after occlusion and 8 hours and 16 hours later (a total of three times). Twenty-four hours after occlusion, each of the treated rats was sacrificed, and the brain was excised, stained with TTC and cut into equal six parts from top to bottom. The cross-sections were photographed, and the ratio of infarcted areas to the whole brain was measured by means of a planimeter. The result is shown in Table 3.

TABLE 3

| Compound No. | Number of Animals Tested | Rate of Infarcted Area (%) |
|---|---|---|
| Control group | 9 | 11.58 ± 0.81 |
| 1 | 10 | 5.03 ± 0.49** |
| 7 | 9 | 6.96 ± 0.79* |
| 17 | 9 | 8.01 ± 0.54* |
| 28 | 9 | 5.79 ± 0.43** |
| 31 | 9 | 7.93 ± 0.56* |
| 34 | 9 | 8.56 ± 0.71* |
| 59 | 8 | 7.69 ± 0.67* |

*5% significant difference
**1% significant difference

EXAMPLE 40

(Tablets containing 1-(3-pyridylcarbonyl)-5-phenyl-2-pyrazoline as active ingredient)

An intimate mixture of 45 g 1-(3-pyridylcarbonyl)-5-phenyl-2-pyrazoline, 42 g lactose, 45 g corn starch and 25 g crystalline cellulose was kneaded and granulated using an aqueous solution of 5 g hydroxypropylcellulose, and the granules thus obtained were dried at 50° C. for four hours, mixed with 3 g magnesium stearate, and shaped into tablets (each weighing 200 mg) with a tablet machine.

EXAMPLE 41

(Injections containing 1-(3-pyridylcarbonyl)-5-methyl-2-pyrazoline as active ingredient)

1-(3-pyridylcarbonyl)-5-methyl-2-pyrazoline (0.3 g) was dissolved in 10 ml of 0.9% physiological saline, and the solution was sealed in a 10-ml ampule, giving an aqueous parenteral injection.

The solution prepared above may be used for transfusion by diluting it with 200 ml of 0.9% physiological saline or by dissolving it in 200 ml of 10% glycerol solution.

EXAMPLE 42

(Suppositories containing 1-(3-pyridylcarbonyl)-5-butyl-2-pyrazoline as active ingredient)

1-(3-Pyridylcarbonyl)-5-butyl-2-pyrazoline (10 g) was dissolved in 9 g Witebsol ® (Dinamit Nobel Chemicals, West Germany) by heating at 60° C., the homogeneous mixture thus obtained was cast into a mold (each piece weighing 1.5 g or 3 g) and solidified by cooling, giving suppositories.

What is claimed is:

1. A 2-pyrazoline derivative represented by the formula (A):

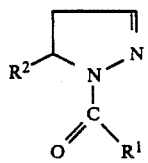

wherein $R^1$ is a pyridyl, pyridyl, pyrazyl or an alkoxyl group; and $R^2$ is a hydrogen atom, an alkyl, a pyridyl, a furyl, phenyl or a substituted phenyl group.

* * * * *